United States Patent [19]

Yanase

[11] Patent Number: 4,600,104
[45] Date of Patent: Jul. 15, 1986

[54] BAG FOR MOTHER'S MILK

[76] Inventor: Shozaburo Yanase, 2-20, Tsurigane-cho, Higashi-ku, Osaka, Japan

[21] Appl. No.: 561,975

[22] Filed: Dec. 16, 1983

[30] Foreign Application Priority Data

Jun. 8, 1983 [JP] Japan .............................. 58-87257[U]

[51] Int. Cl.⁴ ........................ B65D 33/16; B65D 33/38
[52] U.S. Cl. .................................. 206/604; 206/484;
215/11 E; 383/35; 383/61; 383/91; 383/112;
383/113; 383/908
[58] Field of Search ................... 383/35, 113, 112, 91,
383/61, 908; 215/11 E; 206/484, 604

[56] References Cited

U.S. PATENT DOCUMENTS

| 2,197,490 | 4/1940 | Williams et al. | 383/91 |
|---|---|---|---|
| 2,200,313 | 5/1940 | Volksdorf | 383/91 |
| 2,773,285 | 12/1956 | Piazze et al. | 383/37 |
| 2,866,488 | 12/1958 | Thompson | 383/37 |
| 2,935,241 | 5/1960 | Brady | 383/37 |
| 2,990,101 | 6/1961 | Mead et al. | 383/906 |
| 2,999,533 | 12/1961 | Slagel et al. | 383/35 |
| 3,186,625 | 6/1965 | Mead et al. | 383/906 |
| 3,189,253 | 6/1965 | Mojonnier | 383/35 |
| 3,321,125 | 5/1967 | Quackenbush et al. | 383/35 |
| 3,448,915 | 6/1969 | Schwarzkopf | 383/37 |
| 3,520,471 | 7/1970 | Faust | 383/908 |
| 3,625,351 | 12/1971 | Eisenberg | 206/484 |
| 3,762,542 | 10/1973 | Grimes | 383/37 |
| 3,822,806 | 7/1974 | Grimes | 383/37 |
| 3,865,304 | 2/1975 | Mojonnier et al. | 383/91 |

FOREIGN PATENT DOCUMENTS 1239600  7/1971  United Kingdom .............. 215/11 E Primary Examiner—Stephen P. Garbe
Attorney, Agent, or Firm—Oblon, Fisher, Spivak, McClelland & Maier

[57] ABSTRACT

A bag for the preservation of mother's milk made of a laminated film or laminated tube obtained from an extrusion molding, wherein said bag comprises sealing portion(s) provided on the side(s) of the bag and extended in the transverse direction to the direction of said extrusion, and notches provided on the sealing portion(s) at the direction of said extrusion in order to open the bag along the direction of the extrusion, the bag being hermetically or tightly sealed while substantially containing nothing therein.

10 Claims, 13 Drawing Figures

BAG FOR MOTHER'S MILK

DETAILED DESCRIPTION OF THE INVENTION

The present invention relates to a bag for the preservation of mother's milk and, more specifically, it relates to a bag for mother's milk made of a laminated film or laminated tube prepared through extrusion molding for preserving the mother's milk under the frozen state. The "mother's milk" according to the present invention means breast milk which is milk from the woman breast.

The bag for the preservation of the mother's milk is constructed such that it is served for users in the form of a hermetically or tightly sealed bag which substantially contains nothing to the inside of the bag and the users can easily open the sealed bag at one end for filling the mother's milk to the inside.

The importance of the mother's milk for the sake of growing up a baby has been re-estimated in recent years, particularly, in dietetical and immunological points of view. With the wide spread use of refrigerators equipped with freezer it has become possible, in a case where a mother can not directly give her milk to a baby, to conserve mother's milk under the frozen state in said freezer after putting the mother's milk collected by the use of a breast pump as disclosed in U.S. Pat. No. 3,977,405 into a suitable container. Then, the mother's milk thus preserved under the frozen state can be defrozen at any desired time and supplied to the baby by the use of a baby's bottle or a feeding bottle as well known.

By the way, it is required for the container of this type intended to be used for preserving the mother's milk under the frozen state in the freezer that the container can be kept at a sterilized state until it is served for filling the mother's milk therein. In addition, it is necessary that the container can be used conveniently and is provided at hand of the user and further that it is, desirably, disposable after the use.

Thin flexible bags made of synthetic resin or the like have heretofore been used as the container for the preservation of the mother's milk but since most of such bags are usually opened at one end thereof, they involve a difficulty in keeping the inside of the bag at the sterilized state.

The first object of the present invention is to provide a bag for mother's milk which is made of a laminated film or laminated tube in order to preserve the mother's milk contained in the bag under the frozen state, usually hermetically sealed until the bag is actually used for the preservation of the milk therein and can be opened at one end thereof upon containing the milk in the bag without using particular means such as scissors. The hermetically sealed bag is exposed to the gamma ray irradiation for sterilization of the inside and can be kept at a sanitary state.

The second object of the present invention is to provide a bag for the preservation of the mother's milk made of a laminated film or laminated tube in which the inner layer of the bag tends to elongate more readily than the outer layer of the bag for easier filling of the mother's milk in the bag when it is opened, thereby the opening periphery of the bag being turned or bended outwardly near the opened portion due to the greater elongation rate of the inner layer than that of the outer layer to facilitate the filling of the mother's milk in the bag.

The third object of the present invention is to provide a bag for the preservation of the mother's milk which is further combined with means for closing said open portion of the bag again after the bag has been opened and the mother's milk has been filled in the bag. In addition, closure for the open portion of the bag by the above-mentioned closing means can further be facilitated by preliminarily closing the bag at the position near the level of the milk in the bag with a preliminary closing means prior to the closure of the opened portion by said closing means.

In aspect of the present invention, there is provided a bag for the preservation of the mother's milk made of a laminated film or laminated tube prepared by extrusion molding, wherein said bag comprises a sealing portion(s) provided on at at least one side of the bag and extended in the transverse direction to the direction of said extrusion, and at least a notch provided on the sealing portion and directed to the same or opposite direction of said extrusion for opening the one end of the bag along or opposite to the direction of extrusion, the bag being hermetically or tightly sealed.

Preferably, the bag contains substantially nothing to the inside thereof in the tightly sealed up state before the bag is actually used.

The foregoing and other features, as well as advantages of the present invention will become clearer by the following descriptions for preferred embodiments in conjunction with the accompanying drawings, in which.

The bag for the preservation of the mother's milk is made of a laminated film or laminated tube obtained from an extrusion molding, wherein said bag comprises sealing portion(s) provided on the side(s) of the bag and extended in the transverse direction to the direction of said extrusion, and notches provided on the sealing portion(s) at the direction of said extrusion in order to open the bag along the direction of extrusion, the bag being hermetically or tightly sealed while substantially containing nothing therein.

Mother's milk is collected by using a breast pump such as disclosed in U.S. Pat. No. 3,977,405 and the mother's milk contained in the breast pump can be put into the bag through said open portion as described above. The bag thus containing the mother's milk therein is closed at the open portion by the closing means and then placed in a freezer or a freezing chamber and said milk is preserved under the frozen state, for example, at a temperature below −18° C. The closing means comprises at least one elongate plate member made of thick paper, board or plastic sheet etc. When the closing means comprises three elongate plates, first, second and third elongate plates, one longer edge of the first elongate plate is foldably connected to the mating longer edge of the second elongate plate, and one shorter edge of the first elongate plate is foldably connected to the mating shorter edge of the third elongate plate. The bag can surely be closed with the closing means by folding the third elongate plate over the first elongate plate to hold the open portion of the bag between the first and the second elongate plates, further folding the second elongate plate over the third elongate plate and, thereafter, winding the portion near the open portion of the bag around the three folded elongate plates by the several turns. Thereafter, an adhesive tape is appended at the closed portion of the bag to closely seal and secure the portion with ease. Each of the three elongate plate members has preferably a same size.

A preliminary closing member such as a clip may be used for preliminarily closing the bag at the position near the level of the milk in the bag prior to the above-mentioned closure by means of the closing means. This can surely prevent the mother's milk contained in the bag from leaking externally and much facilitate or aid the subsequent closure for the open portion made by the closing means, and also can facilitate a removal of air remaining in the bag.

Figure 1:
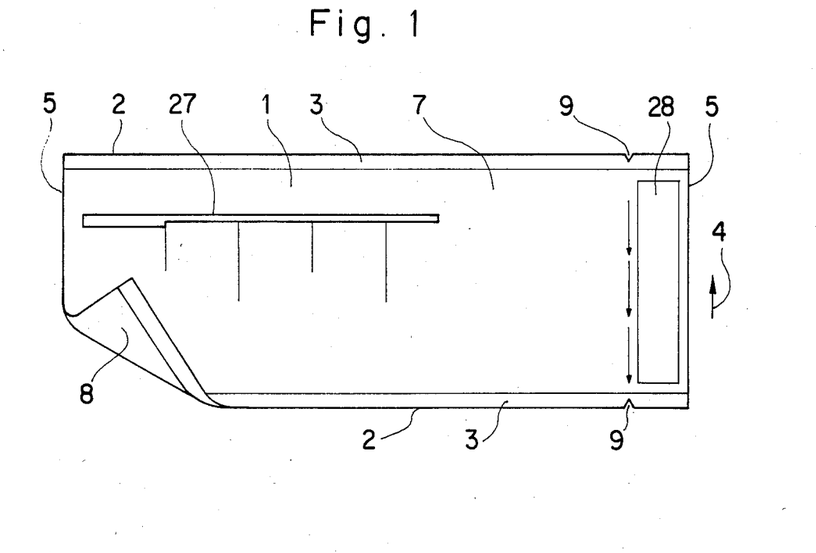
FIG. 1 is an explanatory view showing a preferred embodiment of a bag for the preservation of the mother's milk according to the present invention in which one end of the bag is turned back for showing the upper surface, as well as the lower surface thereof.

In the drawing, a bag for the preservation of the mother's milk generally shown by the reference numeral 1 is made of a laminated tube 10 prepared from extrusion molding by cutting the tube in the transverse direction to the extruding direction at every predetermined length and sealing or welding each of cut edges 2, 2 by means of heat seal. The sealing portions or the welding portions 3, 3 thus formed for sealing up the bag 1 are extended in the direction substantially perpendicular to the direction of an arrow 4 which represents the extruding direction of the laminated tube 10. The bag 1 is of a generally rectangular shape defined with the cut edges 2, 2 and lateral edges 5, 5 as both ends. The lateral edges 5, 5 are already closed upon molding of the laminated tube 10 and defined by folding the lateral ends of the laminated tube 10 between pinch rollers 6, 6 (refer to FIG. 4). In other words, the bag 1 comprises an upper surface 7 and a lower surface 8 integrally connected to each other at the lateral edges 5, 5 upon molding and is hermetically or tightly sealed by sealing the upper surface 7 and the lower surface 8 at the sealing portions or welding portions 3, 3. Although a little amount of air may be left or remained within the bag 1 after said sealing step, it is preferred that the bag is sealed up so tightly as containing substantially nothing to its inside. Then, the sealed bag 1 is exposed to gamma ray irradiation in order to sterilize the inside of the bag 1.

Notches 9, 9 directed along and opposite to the direction of the arrow 4 are provided on the sealing portions or the welding portions 3, 3 at the position close to the one of the lateral edges 5.

Figure 3:
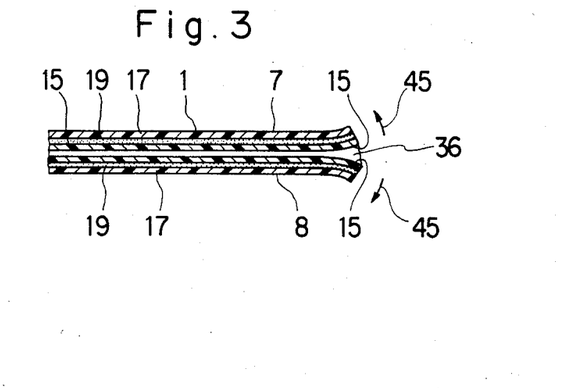
FIG. 3 is an enlarged cross sectional view taken along line III—III in FIG. 2.
Figure 4:
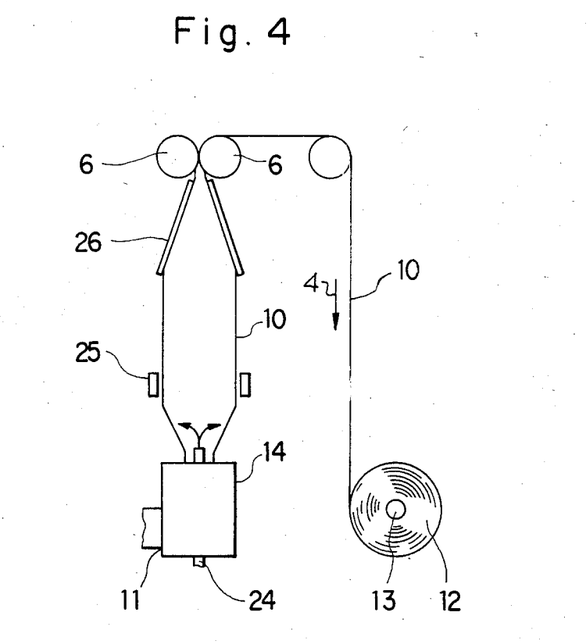
FIG. 4 is an explanatory view of the apparatus for producing a laminated tube.
Figure 5:
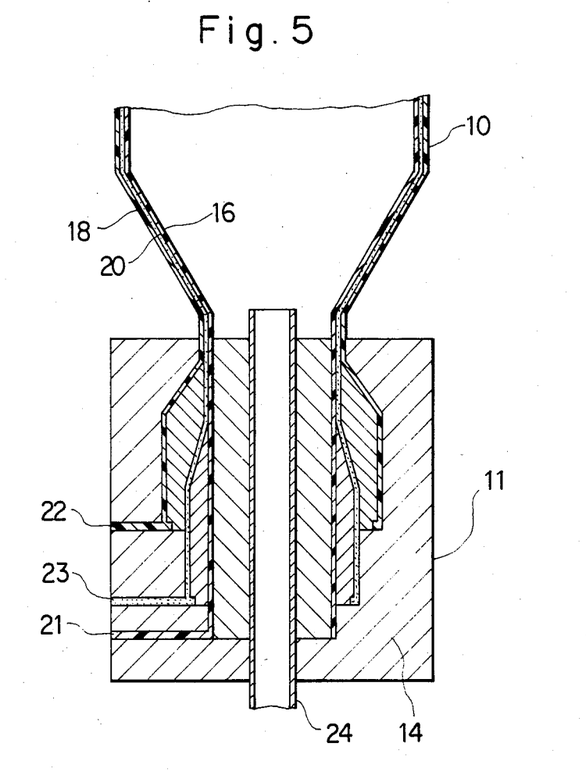
FIG. 5 is an enlarged cross sectional view for a part of the apparatus shown in FIG. 4.

As shown in FIG. 4, a molding apparatus for producing the laminated tube 10 comprises an extruder 11 and a take-up apparatus 12 for taking-up the laminated tube 10 extruded from the extruder 11 by way of pinch rollers 6, 6. The laminated tube 10 extruded from the extruder 11 is inflated into a thin tubular laminate by the air blown into the tube by way of a conduit 24 and then taken-up around a take-up roller 13 of the take-up apparatus 12 while being pulled so as to slightly elongate in the extruding direction corresponding to the arrow 4 by the pinch rollers 6, 6 and then folded between the rollers. The laminated tube 10 comprises, of which plurality of the bags 1 are made, a first layer 16 as an inner layer 15 of the bag 1, a second layer 18 as an outer layer 17 of the bag 1 and an adhesive layer 20 as an intermediate layer 19 (adhesive layer) between the inner layer 15 and the outer layer 17 (refer to FIG. 3 and FIG. 5). Correspondingly, the die 14 in the extruder 11 comprises, as shown in FIG. 5, passageways 21, 22 and 23 for molten thermoplastic resins forming the first layer 16, the second layer 18 and the adhesive layer 20 respectively. The conduit 24 extended in the axial direction in the die 14 is communicated with a pressurized air source (not shown) for inflating the laminated tube 10. A cooling device 25 is disposed between the die 14 and the pinch rollers 6, 6, and a guide plate 26 is disposed at the upstream of the pinch rollers 6, 6 for guiding the laminated tube 10 to the gap between the pinch rollers 6, 6 so that the laminated tube 10 may preferably be folded by the pinch rollers 6, 6.

It is necessary that the inner layer 15 for the bag 1 has good barrier against moisture transmission and water proofness and a flexibility, as well as it should be chemically stable giving no substantial effects on the mother's milk to be contained in the inside of the bag. Accordingly, a polyethylene is employed, for instance, as a thermoplastic resin material forming the first layer 16 of the tube 10. On the other hand, it is necessary that the outer layer 17 of the bag 1 has heat and cold resistant properties and a flexibility, as well as it should be less than gas permeable and have oil-resistance and chemical stability. Accordingly, a nylon is employed, for instance, as the thermoplastic resin material forming the second layer 18 of the tube 10. Furthermore, as described below, it is required for the inner layer 15 that it has a larger elongation rate than that of the outer layer 17. This requirement can be satisfied well by forming the inner layer 15 with polyethylene and the outer layer 17 with nylon. The intermediate layer 19 is an adhesive layer for bonding the inner layer 15 with the outer layer 17. The bag 1 is formed as a transparent or translucent and thin body.

An appropriate scale 27 is printed on the upper surface 7 of the bag 1 for measuring the volume of the mother's milk contained in the bag 1, by which the user of the bag 1 can easily recognize the amount of the mother's milk contained in the bag 1. Furthermore, notices upon using the bag 1 or the likes are printed over the upper surface 7. For instance, notices indicating the method of opening the bag 1 are printed on a space 28 between the lateral edge 5 and the notches 9, 9 of the bag 1.

Figure 2:
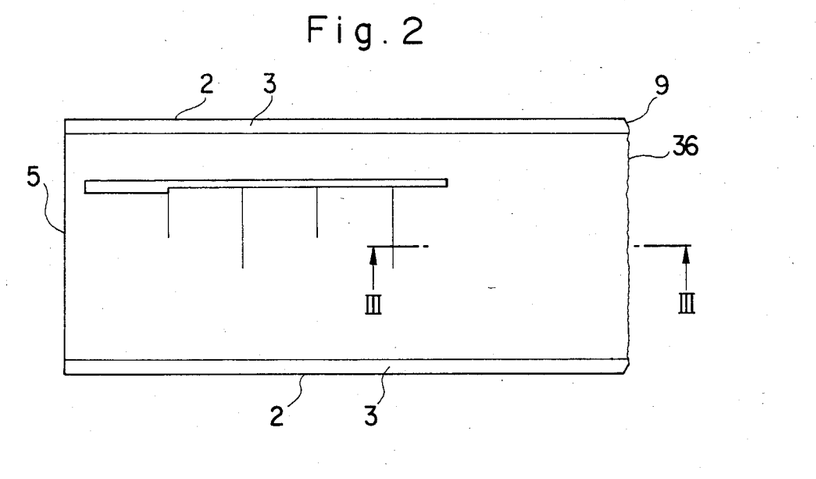
FIG. 2 is a plan view of the bag shown in FIG. 1 after opening the bag.

The hermetically sealed bag 1 for the preservation of the mother's milk can be easily opened by tearing it off at the notch 9 formed at the welding portions 3, 3 (refer to FIG. 2).

Figure 6:
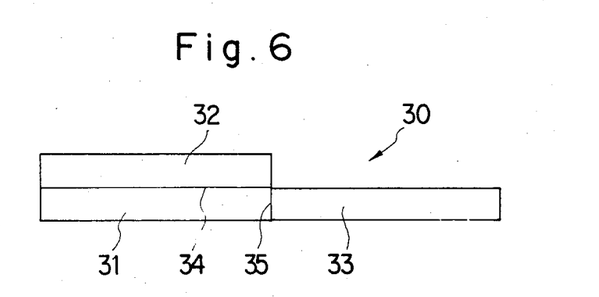
FIG. 6 is a plan view for a specific embodiment of a closing means.

FIG. 6 shows a closing means 30 for closing the bag 1 opened at one end 36 through which the mother's milk is filled in the bag 1. The closing means 30 comprises three elongate plates 31, 32 and 33 each of a rectangular configuration. Each of the plates 31, 32 and 33 of substantially the same size has a length greater than the width or the size between the sealing portions or the welding portions 3, 3 of the bag 1, and is made of thick paper such as a cardboard or a plastic sheet. A longer folding line 34 is formed between the longer edge of the plate 31 and the mating longer edge of the plate 32, so that the plates 31 and 32 are foldably connected to each other by way of the longer folding line 34. A shorter folding line 35 is formed between the shorter edge of the plate 31 and the mating shorter edge of the plate 33, so that the plates 31 and 33 are foldably connected to each other by way of the shorter folding line 35.

Figure 7:
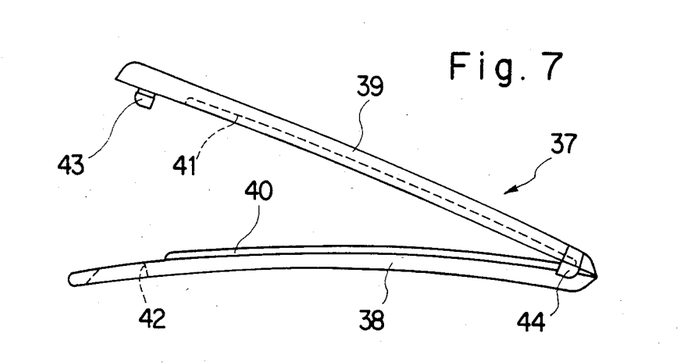
FIG. 7 is a side view for a preliminary closing means.
Figure 8:
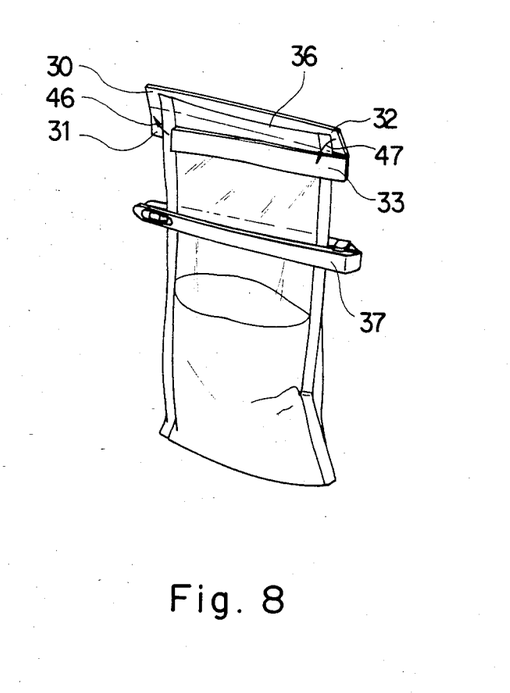
FIG. 8 and FIG. 9 are explanatory views for the closing method upon closing the open portion of the bag.

FIG. 7 shows a preliminary closing means 37 for preliminarily closing the opened bag at the position near the level of the milk in the bag 1 before closing the open portion 36 by means of the closing means 30. The preliminary closing means 37 comprises a plastic clip composed of a lower clipping member 38 and an upper clipping member 39 hinged at one end to each other. An elongate ridge 40 and an elongate groove 41 in a complementary shape are provided respectively on the opposing surfaces of the lower clipping member 38 and the upper clipping member 39. The length for the ridge 40 and the groove 41 is greater than said width of the bag 1. A conversely tapered aperture 42 is formed to the other end of the lower clipping member 38 and a protrusion 43 is formed to the other end of the upper clipping member 39 for engaging into the aperture 42 to keep both of the clipping members 38 and 39 in a closed position as shown in FIG. 8. The lower clipping member 38 has a curved configuration for providing the same with a biasing tendency relative to the upper clipping member 39, so that upon disengaging the aperture 42 with the protrusion 43, both of the clipping member 38 and 39 are shifted to open positions as shown in FIG. 7. Guide pieces 44 are integrally connected on both sides at one end of the upper clipping member 39 for guiding the lower clipping member 38 therealong.

In this structure, when the bag 1 is clipped by means of the preliminary closing means 37 at the position near the level of the mother's milk in the bag 1, the bag 1 is surely clipped at said position between the elongate ridge 40 and the elongate groove 41 thereby enabling to prevent the mother's milk contained in the bag 1 from leaking externally.

The total thickness of the laminate having the inner layer 15, the intermediate layer 19 and the outer layer 17 is 50–150 $\mu$m and, preferably, 75–90 $\mu$m. The thickness of the inner layer 15 is 20–50 $\mu$m, preferably, 25–30 $\mu$m, the thickness for the intermediate layer 19 is 15–50 $\mu$m, preferably, 25–30 $\mu$m and the thickness for the outer layer 17 is 15–50 $\mu$m, preferably, 25–30 $\mu$m.

The inner layer 15 as the first layer 16 may be made of transparent low density polyethylene, transparent medium density polyethylene, transparent high density polyethylene, transparent linear low density polyethylene or transparent polypropylene.

The outer layer 17 as the second layer 18 may be made of transparent nylon 6, transparent nylon 6-6, transparent copolymer of nylon 6 and nylon 6-6, transparent polymer or copolymer of vinylidene chloride resin or transparent Eval.

The intermediate layer 19 as the adhesive layer 20 may be made of a modified polyolefin resin.

In the use of the bag 1 for the preservation of the mother's milk having the foregoing structure, one end of the bag is opened through the notches 9, 9 for filling in the bag 1 with the mother's milk which has been collected by a breast pump such as disclosed, for instance, in U.S. Pat. No. 3,977,405.

The bag 1 is provided with the sealing portions or the welding portions 3, 3 in the direction perpendicular to the direction of the arrow 4, that is, the direction of extruding the laminated tube 10 and formed with the notches 9, 9 in the vicinity of one of the edges 5, 5 at the sealing portion or the welding portions 3, 3. Since the notches 9, 9 are oriented respectively along and opposite to the direction of the arrow 4, the bag 1 can be opened with ease at one end thereof through the notch 9 by picking-up two portions near one of the notches and pulling one of said two portions in the direction toward the other of the notches the two portions being both side portions of the notch 9 on the sealing portion or the welding portion 3. Since the laminated tube 10 has been pulled so as to be slightly elongated in the extruding direction by the pinch rollers 6, 6 upon molding of the laminated tube 10, the bag 1 can be torn or broken with rather ease in the direction perpendicular to the arrow 4. Accordingly, it is no more necessary to use scissors or like other cutting tools upon opening the bag 1 and the fear of contaminating the open portion 36 of the bag 1 with the blade surface of the scissors or the likes can surely be avoided.

In addition, since the inner layer 15 is made of material, for example, polyethylene with a greater elongation rate than that of the outer layer 17 which is made, for example, of nylon, the inner layer 15 exhibits a greater elongation than the outer layer 17, upon tearing the one end of the bag 1 through the notch 9, whereby the upper surface 7 and the lower surface 8 are turned or bent outwardly in the direction of the arrows 45 at the opened end 36 of the bag 1, as shown in FIG. 3. Consequently, this can extremely facilitate the operation of filling the mother's milk through the open portion 36 to the inside of the bag 1. Specifically, the mother's milk contained in the breast pump can be easily put into the bag 1 by inserting the open end of the breast pump to said open portion 36 where the upper surface 7 and the lower surface 8 are outwardly turned so as to apart from each other in the direction of the arrow 45. The breast pump and the periphery of the open end thereof are previously kept clean.

Figure 9:
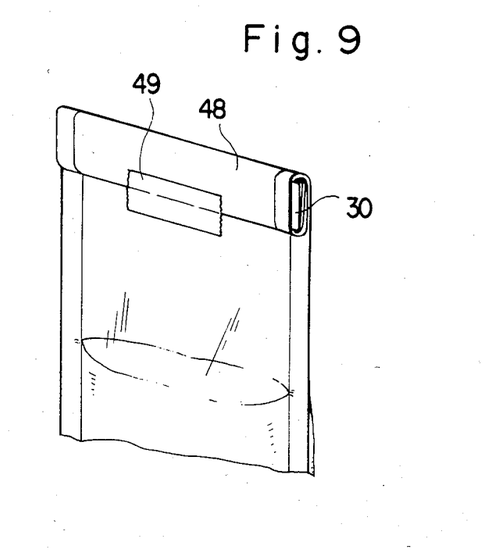

After filling the mother's milk in the bag 1, the portion of the bag 1 which is situated slightly above the level of the milk in the bag 1 is clipped by the preliminary closing means 37 and air remaining in the bag 1 is removed from the inside of the bag 1, thereafter, the bag is closed by the closing means 30 (refer to FIG. 8). The elongate plate 33 is folded over the elongate plate 31 along the shorter folding line 35 in the direction of the arrow 46 so as to put the portion near the open portion 36 of the bag 1 therebetween. Then, the elongate plate is further folded thereover along the longer folding line 34 in the direction of the arrow 47 so as to put the open portion between the plates 32, 33, thereafter, the portion near the open portion 36 of the bag 1 is wound by several turns around the three plates 31, 32 and 33 folded to each other, whereby the bag 1 can surely be closed (refer to FIG. 9). Then, the adhesive tape 49 is appended over the closed portion 48 of the bag 1 thus formed, by which the closed portion 48 can be secured or fixed with ease. The adhesive tape 49, desirably, a non-toxic and cold-working tape comprises a substrate made of a plastic film such as a polyester resin having predetermined strength, flexibility and cold resistance, and adhesives not solidifying at low temperature, disposed on the substrate. In above operation, it is possible to facilitate the removal of air remaining in the bag 1 owing to the preliminary closing means 37.

The bag 1 filled with the mother's milk and closed with the closing means 30 is written with the date of fillage or the like on the upper surface 7 and, thereafter, can be preserved under the frozon state in the freezing chamber of a refrigerator or the like. The mother's milk thus preserved under the frozen state within the bag 1 can be taken out as desired from the freezing chamber and can easily be defrozen by immersing the bag into the water. The defrozen mother's milk is transferred from the bag 1 to a known baby's bottle of feeding bottle, through which it can be applied to the baby with ease. The bag 1 and the closing means 30 are discarded or thrown away after the use. U.S. Pat. No. 3,977,405 as described above discloses a breast pump equipped with a baby's bottle by which the milk can be applied to the baby.

Figure 10:
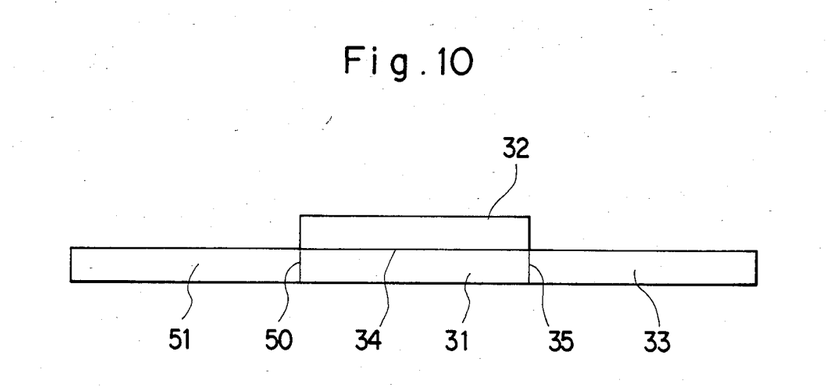
FIG. 10 is a plan view for another specific embodiment of the closing means.

Although the closing means 30 comprises three elongate plates 31, 32 and 33 each of the same size and having the length greater than the width of the bag 1 in the previous embodiment, the length for the elongate plate 33 may be made shorter. Said closing means may be made of two elongate plates 31, 32 by omitting the plate 33 or may be made of only one elongate plate 31 by omitting the plate 32 and 33. Alternatively, another elongate plate 51 may be provided foldably to the shorter edge of the elongate plate 31 by way of a shorter folding line 50, so that the elongate plates 33 and 51 may be overlapped to each other on the elongate plate 31. The length for the elongate plate 51 may be shorter than the width for the bag 1. The closing means may be made of thin plastic material.

Instead of using such closing means 30, the open side 36 of the bag 1 may be closed simply by an annular rubber string or the like.

Further, while the bag 1 is made of the inner layer 15, the outer layer 17 and the intermediate layer 19 as the adhesive layer in the previous embodiment, the bag 1 may be made of two layers by using the known method of bonding the inner and the outer layers directly together.

Figure 11:
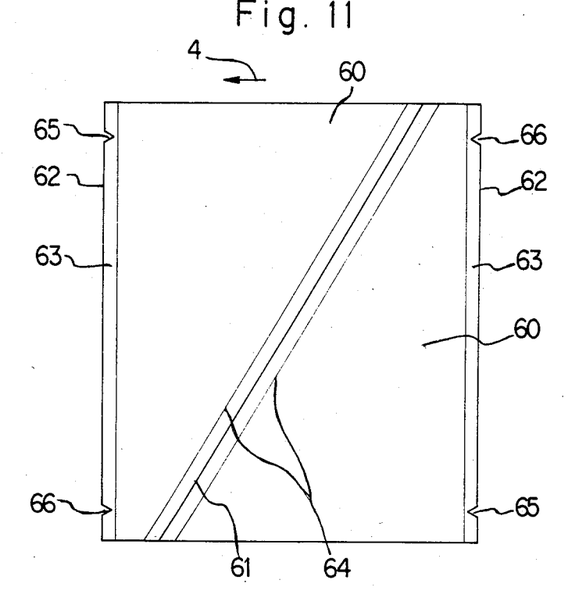
FIG. 11 is a plan view for another preferred embodiment of the bag for the preservation of the mother's milk according to the present invention.

In addition, although the bag 1 is formed as a rectangular shape in the previous embodiment, the bag may be in a triangular shape or in a trapezoidal shape. FIG. 11 shows two bags cut out from the laminated tube 10 in which bags 60, 60 can easily be separated from each other along an oblique cutting line 61. Sealing or welding portions 63, 63 are formed along cut edges 62, 62 extending in the perpendicular direction to the direction of extruding the laminated tube 10 corresponding to the arrow 4, and oblique sealing or welding portions 64, 64 extending along the cutting line 61 between the sealing or welding portions 63, 63. Each of the bags 60 is formed so as to be hermetically sealed between the sealing or welding portion 63 and the oblique sealing or welding portion 64, and notches 65, 66 are formed to the upper and lower end for each of the bags 60. Upon opening the bag 60, the bag is torn at one end thereof induced by the notch 65. After filling the mother's milk in the bag 60, the open portion of the bag 60 can be closed with ease by the use of the preliminary closing means 37 and the closing means 30. The notch 66 is formed for opening the other end of the bag 60 upon transferring the mother's milk having been preserved within the bag 1 under the frozen state into the baby's bottle after defreezing. Since the other end of the bag opened through the notch 66 is narrowed toward the top, the mother's milk in the bag 60 can easily by transferred into the baby's bottle. A notch may also be formed to the other end opposing to the open portion 36 of the bag 1 in the previous embodiment so as to open the other end through the notch and transfer the mother's milk in the bag 1 into the baby's bottle.

Figure 12:
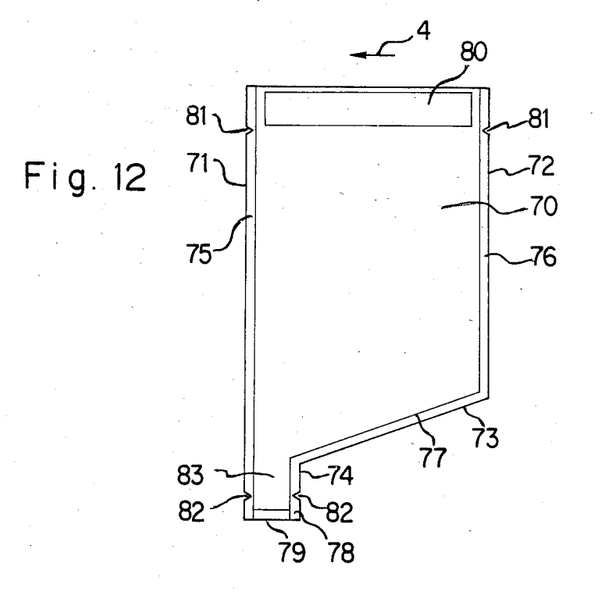
FIG. 12 is a plan view for a further embodiment of the bag for the preservation of the mother's milk according to the present invention.

FIG. 12 shows a bag 70 which is a further modified embodiment of the bag 1. The bag 70 is formed from the laminated tube 10 by cutting the tube along both of cut edges 71, 72 and further cutting along an oblique edge 73 extended obliquely from the lower end of the cut edge 72 and a downward edge 74 extended from the lower end of the oblique edge 73 downwardly substantially in the perpendicular direction to the arrow 4. The bag 70 is hermetically sealed by forming sealing or welding portions 75, 76, 77 and 78 along the cut edges 71, 72, the oblique edge 73 and the downward edge 74. A sealing or welding portions 79 extended between the sealing or welding portions 75 and 78 may be provided to the lower end of the bag 70. Notches 81, 81 are formed at the upper end of the sealing or welding portions 71, 72 at positions lower than a space 80 which corresponds to the space 28, while notches 82, 82 are formed at the lower ends of the sealing or welding portions 75, 82. One of the notches 81, 81 or one of the notches 82, 82 may be omitted. The notch 81 is formed for opening the upper end of the bag 70 upon filling the mother's milk to the inside of the bag 70 and the notch 82 is formed for opening the lower end of the bag 70 upon transferring the mother's milk in the bag 70 into the baby's bottle. The positions for the downward edge 74 and the sealing or welding portion 78 are selected so as to define the discharging port 83 between the sealing or welding portions 75, 78, in such a way that the size of the discharging port 83 is slightly smaller than the diameter for the opening end of the baby's bottle. The notices upon opening the upper end of the bag 70 through the notch 81 are printed on the space 80 and a scale is printed on the upper surfaces of the bag 70 in the same manner as in the bag 1. Similar printings may be also applied on the bag 60.

Figure 13:
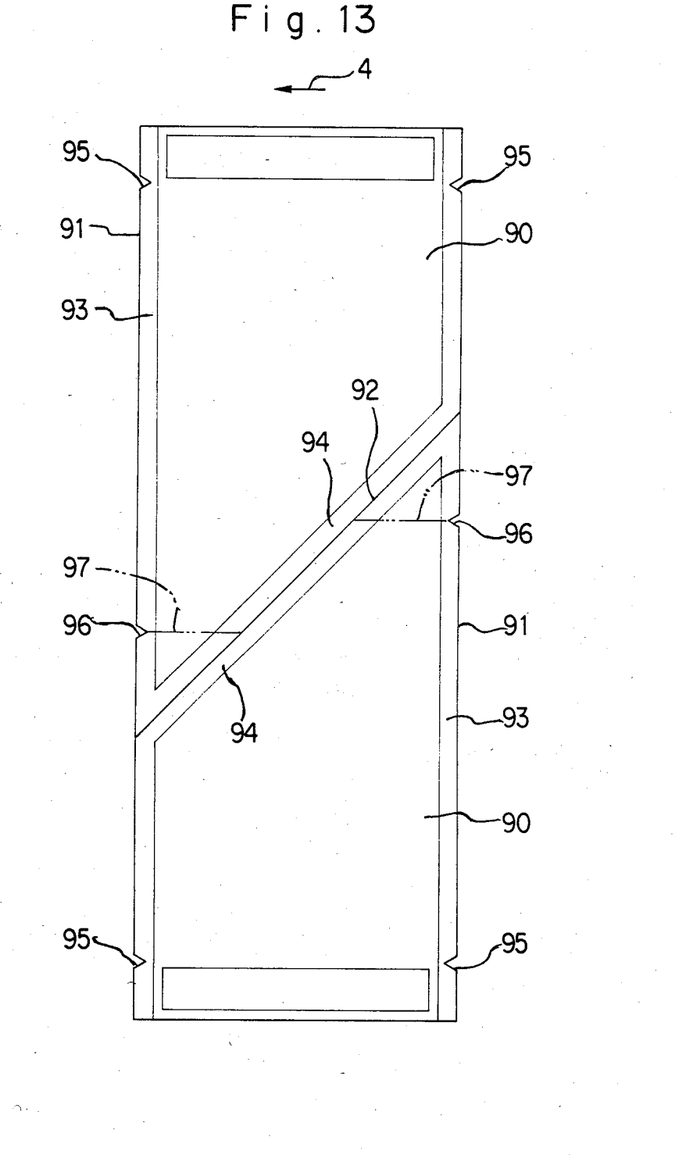
FIG. 13 is a plan view for a still further embodiment of the bag for the preservation of the mother's milk according to the present invention.

FIG. 13 shows two bags 90, 90 which are further more modified embodiment of the bag 1. The bag 90, 90 are formed from the laminated tube 10 by cutting the tube along both of cut edges 91, 91, and further cutting along an oblique edge 92 extended obliquely between said two bags 90, 90. The bag 90 is hermetically sealed by forming sealing or welding portions 93, 93 and 94 along the cut edges 91, 91 and the oblique edge 92. Notches 95, 95 are formed at the upper or lower end of the sealing or welding portions 93, 93 at positions lower than a space which corresponds to the space 28, while notch 96 is formed at the lower or upper position of the welding portion 93. One of the notches 95, 95 may be omitted. The notch 95 is formed for opening the upper or lower end of the bag 90 upon filling the mother's milk to the inside of the bag 90 and the notch 96 is formed for opening the lower or upper end of the bag 90 upon transferring the mother's milk in the bag 70 into the baby's bottle. The angle of the oblique edge 92 and the sealing or welding portion 94 are selected so as to define the discharging port 97 between the sealing or welding portions 93, 94, in such a way that the size of the discharging port 97 is slightly smaller than the diameter for the opening end of the baby's bottle. The notices upon opening the upper end of the bag 90 through the notch 95 are printed on said space and a scale is printed on the upper surfaces of the bag 90 in the same manner as in the bag 1.

Although the bags 1, 60, 70 are made of the laminated tube 10, they can be made of known laminated film which is heat-sealed or welded along the outer circumference thereof to constitute a hermetically sealed bag. Further, the bag may be made of a two or more layered laminate.

As described above, since the bag for the preservation of the mother's milk according to the present invention is made of a laminated tube or laminated film prepared by extrusion molding, it can sufficiently satisfy various properties required as the bag for mother's milk, such as cold resistance, water proofness and strength. Furthermore, since the bag is extended in the perpendicular direction to the direction of extrusion and comprises sealing portion at the side of the bag for hermetically sealing the bag and notch provided on the sealing or welding portion so that the bag is opened along or opposite to the extruding direction, the one end of the bag can be opened with rather ease along the extrusion direction, being induced from the notch. Accordingly, the present invention can provide a bag for the preservation of the mother's milk capable of maintaining the inside thereof clean by the irradiation of the gamma rays under the sealed up state, can be opened with ease at one end upon containing the mother's milk therein and can be thrown away after the use.

What is claimed is:

1. A bag for the hygienic preservation and storage of mother's milk in a frozen state, which bag permits the frozen mother's milk to be thawed and to be transferred hygienically and conveniently to a baby bottle, said bag comprising:
   (a) a first surface and a second surface which are joined together around the peripheries thereof to define a closed interior volume which, prior to use of the bag, is at least substantially empty;
   (b) said first and second surfaces each being formed from a laminated material comprising at least an inner layer and an outer layer adheringly attached to the inner layer, the inner layer of said first and second surfaces being formed of polyethylene or polypropylene and the outer layer of said first and second surfaces being formed of nylon or vinylidene chloride resin;
   (c) said first and second surfaces having been slightly elongated in one direction after lamination so that both layers of said surface are preferentially tearable in said direction, but the inner layers of said surfaces have a greater elongation rate than the outer layers of said surfaces; and
   (d) at least one tear notch in an edge of said first and second surfaces but not extending to the closed interior volume between said first and second surfaces, said at least one tear notch being parallel to said direction and being located close to an edge of the bag,
   whereby;
   (e) an edge can be easily torn off the bag beginning at said at least one tear notch, giving access to the closed interior volume in order to fill the closed interior volume with mother's milk, and,
   (f) since the inner layers of said surfaces have a greater elongation rate than the outer layers of said surfaces, when an edge is torn off the bag, the first and second surfaces inherently bend outwardly around the opening created by the tear, facilitating the hygenic filling of the bag with mother's milk by inserting a breast pump through the opening into the interior volume.

2. A bag according to claim 1, wherein said first and second surfaces are trapezoidal in shape, each of said first and second surfaces being bounded by two edges that are perpendicular to said direction and at least one edge that is oblique to said direction.

3. A bag according to claim 1, wherein said bag further comprises a discharge port for transferring mother's milk contained in said bag into a baby's bottle, said discharge port:
   (a) being defined by said first and second surfaces, said first and second surfaces being joined together to define a passageway in fluid communication with said interior volume, and
   (b) comprising at least another tear notch in an edge of said first and second surfaces but not extending to said passageway, said at least another tear notch being parallel to said direction,
   whereby said discharge port can be opened by tearing said first and second surfaces at said at least another tear notch, allowing mother's milk contained in said bag to exit said bag through said passageway.

4. A bag according to claim 1, wherein said first and second surfaces each additionally comprise an intermediate adhesive layer that bonds said inner and outer layers together.

5. A bag according to in claim 1, wherein said closed interior volume is sterile prior to use.

6. A bag according to claim 1, wherein said first and second surfaces are rectangular in shape, each of said first and second surfaces being bounded by two edges that are perpendicular to said direction and two edges that are parallel to said direction.

7. A bag according to claim 1, wherein said first and second surfaces are triangular in shape, each of said first and second surfaces being bounded by one edge that is perpendicular to said direction, one edge that is parallel to said direction, and one edge that is oblique to said direction.

8. A bag according to claim 1, wherein said bag further comprises means for closing said bag after mother's milk has been inserted into said interior volume.

9. A bag according to claim 1, wherein said first and second surfaces are generally transparent.

10. A bag according to claim 1, wherein a scale is provided on a part of the outer layer of said first and second surfaces for indicating an amount of the mother's milk contained in the bag.

* * * * *